US00PP18165P2

(12) United States Plant Patent
van Steijn

(10) Patent No.: US PP18,165 P2
(45) Date of Patent: Oct. 30, 2007

(54) ***SCABIOSA* PLANT NAMED 'GRAND STONE'**

(50) Latin Name: *Scabiosa caucasica*
Varietal Denomination: Grand Stone

(75) Inventor: Peter van Steijn, Voorhout (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/454,035

(22) Filed: Jun. 15, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Scabiosa* plant named 'Grand Stone', characterized by its upright and somewhat outwardly spreading plant habit; large inflorescences with violet blue-colored flowers; and good garden performance.

1 Drawing Sheet

Botanical designation: *Scabiosa caucasica.*
Cultivar denomination: 'Grand Stone'.

BACKGROUND OF THE INVENTION

The present invention relates to a new and distinct cultivar of *Scabiosa,* botanically known as *Scabiosa caucasica* and hereinafter referred to by the name 'Grand Stone'.

The new *Scabiosa* is a product of a planned breeding program conducted by the Inventor in Voorhout, The Netherlands. The objective of the breeding program was to create new *Scabiosa* cultivars with large blue-colored inflorescences.

The new *Scabiosa* originated from a cross-pollination made by the Inventor in 2000 in Voorhout, The Netherlands, of the *Scabiosa caucasica* cultivar Clive Greaves, not patented, as the female, or seed, parent with an unnamed selection of *Scabiosa caucasica,* not patented, as the male, or pollen, parent. The new *Scabiosa* was discovered and selected by the Inventor as a single flowering plant within the progeny of the stated cross-pollination in a controlled environment in Voorhout, The Netherlands in 2001.

Asexual reproduction of the new *Scabiosa* by micro cuttings in a controlled environment in Voorhout, The Netherlands since 2001, has shown that the unique features of this new *Scabiosa* are stable and reproduced true to type in successive generations.

SUMMARY OF THE INVENTION

The cultivar Grand Stone has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Grand Stone'. These characteristics in combination distinguish 'Grand Stone' as a new and distinct cultivar of *Scabiosa:*

1. Upright and somewhat outwardly spreading plant habit.
2. Large inflorescences with violet blue-colored flowers.
3. Good garden performance.

Plants of the new *Scabiosa* differ from plants of the female parent, the cultivar Clive Greaves, primarily in inflorescence size as plants of the new *Scabiosa* have larger inflorescences than plants of the cultivar Clive Greaves. Plants of the new *Scabiosa* differ from plants of the male parent selection primarily in inflorescence color as plants of the male parent selection have white-colored inflorescences.

Plants of the new *Scabiosa* can be compared to plants of the cultivar Ultra Violet, disclosed in U.S. Plant Pat. No. 14,038. Plants of the new *Scabiosa* differ from plants of the cultivar Ultra Violet primarily in inflorescence color as plants of the cultivar Ultra Violet have darker-colored inflorescences.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Scabiosa.* The photograph is a close-up view of typical inflorescences of 'Grand Stone'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown in Voorhout, The Netherlands, in an outdoor nursery and under conditions which closely approximate commercial production conditions. During the production of the plants, day temperatures ranged from 14° C. to 32° C. and night temperatures ranged from 6° C. to 14° C. Plants of the new *Scabiosa* were one year old when the photographs and description were taken during the late summer.

Botanical description: *Scabiosa caucasica* cultivar Grand Stone.

Parentage:

*Female, or seed, parent.*—*Scabiosa caucasica* cultivar Clive Greaves, not patented.

*Male, or pollen, parent.*—Unnamed selection of *Scabiosa caucasica,* not patented.

Propagation:

*Type.*—By micro cuttings.

*Time to initiate roots.*—About two weeks at 14° C.

*Root description.*—Fine, fibrous.

*Rooting habit.*—Freely branching.

Plant description:

*Appearance.*—Perennial herbaceous container and garden plant. Upright and somewhat outwardly spreading; broad inverted triangle; open, airy appearance. Inflorescences held above the foliage on long peduncles. Moderately vigorous growth habit.

*Plant height.*—About 77 cm.

*Plant spread.*—About 44 cm.

*Lateral branch description.*—Length: About 37 cm. Diameter: About 5 mm. Internode length: About 21.1 cm. Texture: Sparsely pubescent. Color: 144A; towards the base, occasionally tinged with 187A.

Foliage description:

*Arrangement.*—Basal leaves arranged in a rosette; stem leaves, opposite; basal and stem leaves, sessile.

*Length, fully expanded basal leaves.*—About 23.3 cm.

*Width, fully expanded basal leaves.*—About 3.9 cm.

*Length, fully expanded stem leaves.*—About 17 cm.

*Width, fully expanded stem leaves.*—About 6.6 cm.

*Shape, basal leaves.*—Narrowly obovate.

*Shape, stem leaves.*—Ovate.

*Apex, basal and stem leaves.*—Acute.

*Base, basal and stem leaves.*—Narrowly cuneate.

*Margin, basal leaves.*—Sinuate.

*Margin, stem leaves.*—Sinuate; towards the base, lobed.

*Texture, basal and stem leaves, upper and lower surfaces.*—Smooth, glabrous.

*Venation pattern, basal and stem leaves.*—Pinnate.

*Color, basal and stem leaves.*—Developing and fully expanded foliage, upper surface: 137A; venation, 145C, towards the base, tinged with 183D. Developing and fully expanded foliage, lower surface: 137B; venation, 145B.

Inflorescence description:

*Appearance.*—Terminal inflorescences displayed above and beyond foliage on long peduncles. Flowers arranged acropetally on capitula. Inflorescences not persistent.

*Flowering period.*—Plants flower continuously from July to September in The Netherlands.

*Inflorescence longevity.*—Inflorescences typically last about one week on the plant.

*Fragrance.*—Faint; sweet and pleasant.

*Inflorescence diameter.*—Large, about 8.1 cm.

*Inflorescence depth (height).*—About 2.8 cm.

*Inflorescence buds.*—Length: About 1 cm. Width: About 4 mm. Shape: Obovate. Color: 145A to 145B; towards the base, 145C to 145D.

*Outer flowers.*—Diameter: About 3.5 cm. Depth (height): About 4.1 cm. Petals: Quantity per flower: Five in a single whorl, fused at base. Length: Lower three petals, about 4.1 cm; upper two petals, about 2.4 cm. Width: Lower three petals, about 1.8 cm; upper two petals, about 6 mm. Shape: Spatulate. Apex: Rounded. Margin: Entire; undulate. Texture, upper and lower surfaces: Towards the apex, smooth; towards the base, densely pubescent. Color: When opening, upper surface, lower three petals: 82A; towards the base, 92D. When opening, upper surface, upper two petals: 92D. When opening, lower surface, lower three petals: 91A; towards the base, 91D. When opening, lower surface, upper two petals: 91D. Fully opened, upper and lower surfaces, lower three petals: 91A; towards the base, 91D. Fully opened, upper and lower surfaces, upper two petals: 91D.

*Center flowers.*—Diameter: About 8 mm. Depth (height): About 2 cm. Petals: Quantity per flower: Five in a single whorl, fused at base. Length: About 2.5 cm. Width: About 3 mm. Shape: Oblanceolate. Apex: Broadly acute. Margin: Entire. Texture, upper and lower surfaces: Towards the apex, smooth; towards the base, densely pubescent. Color: When opening, upper surface: 92D; towards the base, 84B to 84C. When opening, lower surface: 91D; towards the base, 84B to 84C. Fully opened, upper and lower surfaces: 91D; towards the base, 84B to 84C.

*Flower bracts.*—Quantity per flower: About five in a single whorl; fused at base. Length: About 7 mm. Width: About 0.3 mm. Shape: Filiform. Apex: Acute. Margin: Entire. Texture, upper and lower surfaces: Smooth, glabrous. Color, upper and lower surfaces: N186A; towards the base, 144B.

*Phyllaries.*—Quantity per inflorescence: About ten in a single whorl. Length: About 3.3 cm. Width: About 7 mm. Shape: Linear. Apex: Acute. Base: Broadly cuneate. Margin: Entire. Texture, upper and lower surfaces: Sparsely pubescent. Color, upper surface: 137A. Color, lower surface: 137B.

*Peduncles.*—Length: About 37.2 cm. Diameter: About 4 mm. Strength: Strong. Angle: Erect to about 25° from vertical. Texture: Sparsely pubescent. Color: 144A.

*Reproductive organs.*—Androecium: Stamens per flower: Four. Filament length: About 1.2 cm. Anther shape: Oblong. Anther length: About 3 mm. Anther color: 72B. Pollen amount: Moderate. Pollen color: 68C. Gynoecium: Pistils per flower: One. Pistil length: About 1.7 cm. Stigma shape: Club-shaped. Stigma color: 155A. Style length: About 1.6 cm. Style color: 91B. Ovary color: 145B.

*Seed/fruit.*—Seed and fruit development have not been observed.

Disease/pest resistance: Under commercial production conditions, plants of the new *Scabiosa* have not been observed to be resistant to pathogens or pests common to *Scabiosa*.

Garden performance: Plants of the new *Scabiosa* have been shown to have good garden performance, to be hardy to USDA Zone 6 and to tolerate temperatures to about 35° C.

It is claimed:

1. A new and distinct *Scabiosa* plant named 'Grand Stone' as illustrated and described.

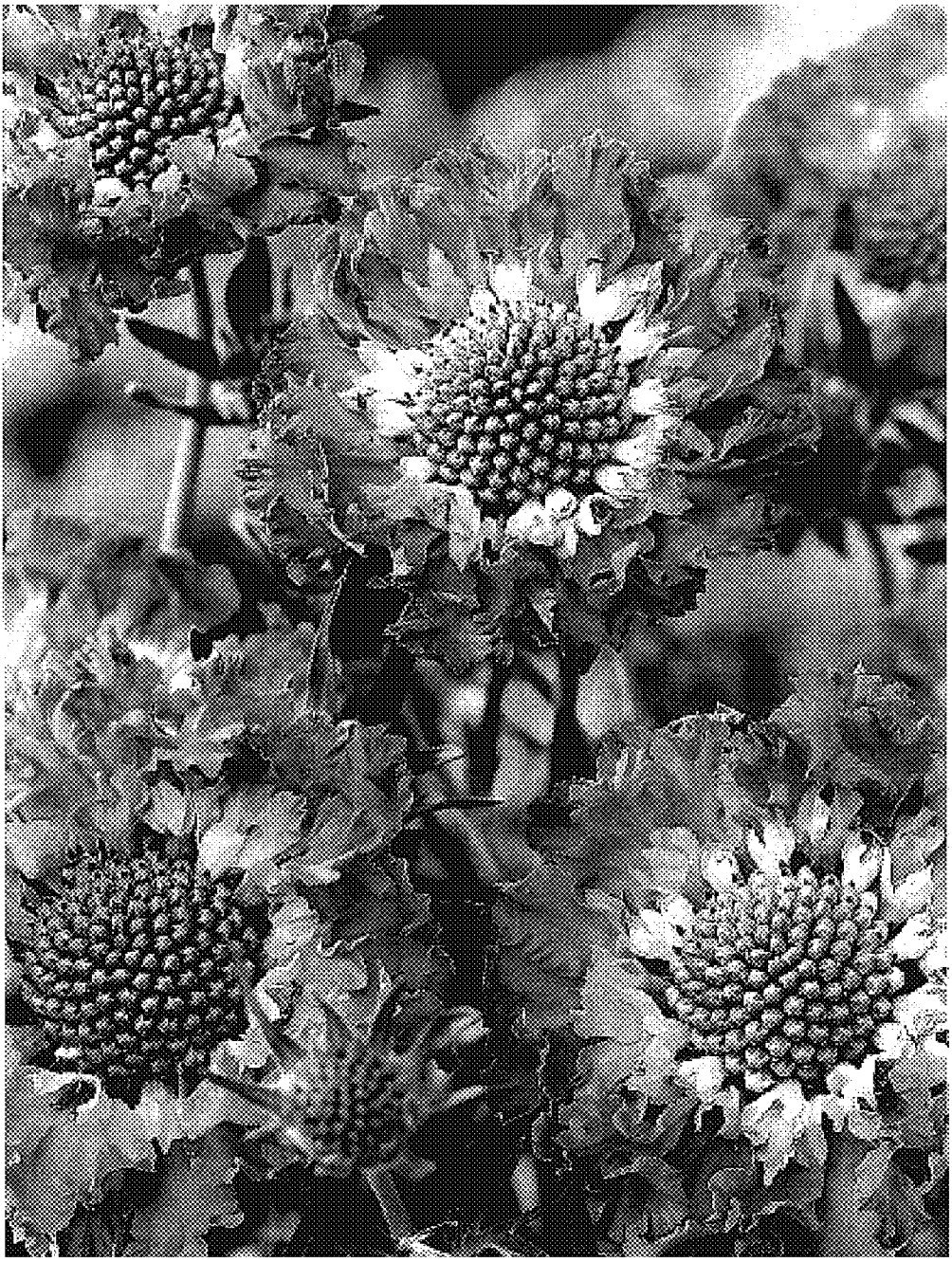

* * * * *